United States Patent [19]
Camilleri et al.

[11] Patent Number: 6,153,170
[45] Date of Patent: Nov. 28, 2000

[54] CHARCOAL-RADIONUCLIDE AGENTS FOR MEASUREMENT OF GASTROINTESTINAL TRANSIT

[75] Inventors: Michael Camilleri; Joseph C. Hung; Brian P. Mullan, all of Rochester, Minn.

[73] Assignee: Mayo Foundation for Medical Education and Research, Rochester, Minn.

[21] Appl. No.: 09/060,551

[22] Filed: Apr. 15, 1998

Related U.S. Application Data

[62] Division of application No. 08/698,209, Aug. 14, 1996, Pat. No. 5,827,497.

[51] Int. Cl.[7] .................................................. A61K 51/12
[52] U.S. Cl. ....................... 424/1.29; 424/1.11; 424/1.25; 424/1.33; 424/1.37
[58] Field of Search .................................... 424/1.25, 1.11, 424/1.29, 1.33, 1.37, 1.65, 456, 489; 534/10, 14; 600/1, 3, 7, 8

[56] References Cited

U.S. PATENT DOCUMENTS 4,657,755   4/1987   Christenson et al. ................... 424/1.11

OTHER PUBLICATIONS

Proano, M., et al. "Transit of Solids through the Human Colon," Am. J. Physiol., 258, G856–G862), 1990.

*Primary Examiner*—S. Mark Clardy
*Assistant Examiner*—Michael G. Hartley
*Attorney, Agent, or Firm*—Schwegman, Lundberg, Woessner & Kluth, P.A.

[57] ABSTRACT

A unit dosage form is provided which comprises an effective amount of a radioisotope adsorbed onto activated charcoal, and which is preferably enterically coated. The unit dosage form is useful for the measurement of intestinal transit.

8 Claims, 4 Drawing Sheets

Simultaneous Measurements of Colonic Transit Using Two Radiolabels
$^{99m}$Tc-charcoal      $^{111}$In-pellets
Anterior
24-hour scan
Posterior
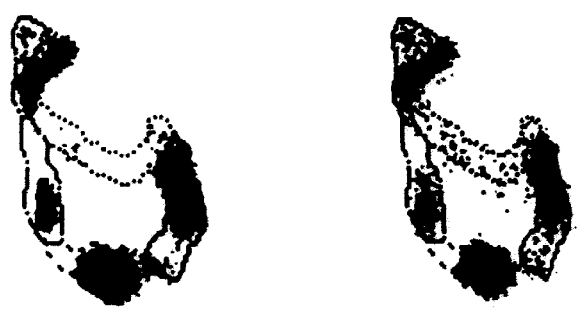
FIGURE 1

CHARCOAL-RADIONUCLIDE AGENTS FOR MEASUREMENT OF GASTROINTESTINAL TRANSIT

CROSS REFERENCE TO RELATED APPLICATION

This application is a divisional of application Ser. No. 08/698,209, filed Aug. 14, 1996, now issued as U.S. Pat. No. 5,827,497, which is incorporated herein by reference.

GOVERNMENT SUPPORT

This invention was developed in part with the assistance of National Institutes of Health Grant No. RR00585. The Government has certain rights in the invention.

BACKGROUND OF THE INVENTION

Disorders of colonic motility are thought to underlie several common clinical problems, yet of all segments of the human gut, motility of the large bowel is least understood. Whereas definitions of normal motility in the esophagus, stomach, and small bowel have allowed regional pathophysiologies to be recognized, normal patterns of motility in the colon are highly variable and poorly defined. Thus, even though several distinctive colonic motor patterns have been described in disease, their relationships with symptoms are unclear.

Measurement of colonic transit is a useful clinical and research technique to evaluate patients with suspected motility disorders of the colon. There are several methods by which colonic transit can be quantified in humans. These approaches include (1) techniques that assess mouth to anus transit, which, however, provide no information on segmental colonic transit; (2) cinefluorography, which is helpful but severely limited by the level of radiation required; (3) the ingestion of radiopaque markers of different shapes with a single or sequential abdominal radiographs; (4) radioisotopic methods, by which liquid radiolabels have been infused into the cecum or splenic fixture. Other radioisotopic methods that have been used include radiolabeled solid markers administered orally either as free particles or enclosed within a capsule. For example, $^{131}$I-labeled cellulose fiber has been used in radioscintigraphic studies of gastric and small bowel transit. See, for example, M. Camilleri et al., *Am. J. Physiol.*, 257, G284 (1989). However, this material is difficult to synthesize, employs a β-radiation source and may be thermally altered when the food carrier is cooked.

These radiological and radioisotopic methods have provided quantitative data on regional colon transit. However, none of these methods are ideal for physiological studies for a number of reasons: some involve intubation and/or preparation of the colon; some evaluate liquid transit in the colon, whereas the movement of particulate matter is probably more relevant. Others do not identify the precise starting point from which colonic transit can be assessed. In particular, the radiopaque marker method, although widely available, inexpensive, and reproducible, requires that the patient is available for four or, more commonly, seven days in order to evaluate the transit profile in the colon by means of two radiographs. Metcalf et al., *Gastroenterology*, 92:40 (1987); Stivland et al., *Gastroenterology*, 101:107 (1991).

The need to have a test with a faster completion time led us to develop a radioscintigraphic approach that has since been simplified and utilized clinically. Proano et al., *Am. J. Physiol.*, 258:G856 (1990).; Camilleri et al., *Gastroenterology*, 103:3 (1992); Charles et al., *Mayo Clin. Proc.*, 70:113 (1995). The method involves radiolabeling ion exchange resin pellets with radioisotopes such as $^{99}$Tc or $^{111}$In and delivering them to the colon in a delayed-release, polymer-coated capsule that dissolves in the alkaline pH of the terminal ileum. However, although initial research studies have shown that these radiolabeled resin pellets are efficacious in measuring colonic transit, there are several constraints on their widespread use.

Specifically, since the resin pellets are not listed in the United States Pharmacopoeia (USP) and are considered to be a new drug moiety, an investigational new drug (IND) application must be filed with the Federal Drug Administration (FDA) prior to their use. In a clinical venue, the IND application and the accompanying requirement of notification of every new project and adverse effect is burdensome and expensive and reduces considerably the cost efficacy of the study. Moreover, and also as a result of the fact that the resin pellets are classified as an investigational drug, there are problems with reimbursement from third-party payers for the clinical use of colonic transit tests.

Therefore, an improved marker for the measurement of colonic transit that overcomes all of the aforementioned drawbacks is needed as such a marker would be extremely useful for diagnostic and physiological studies in health and disease.

SUMMARY OF THE INVENTION

The present invention provides a unit dosage form which is effective to measure gastrointestinal transit in human subjects. The unit dosage form comprises an effective amount of a radioisotope adsorbed on activated charcoal. It is preferred that the radioisotope be one that is widely available and that binds readily to activated charcoal by physical processes such as adsorption. Most preferably, the radioisotope is selected from the group consisting of $^{99m}$Tc, $^{111}$In, $^{201}$Tl, and $^{67}$Ga. Preferably, the unit dosage form, or the charcoal-radioisotope particles within the dosage form, is enterically coated. These unit dosage forms are effective to measure colonic transit.

The present invention also comprises a method of measuring gastrointestinal or colonic motility, said method comprising (a) administering to a subject a unit dosage form comprising an effective amount of a radioisotope adsorbed on activated charcoal and (b) employing scintigraphy to measure the gastrointestinal or colonic transit of said radioisotope. It is preferred that the subject be a mammal, and more preferably, that the subject is a human. It is further preferred that the radioisotope be selected from the group consisting of $^{99m}$Tc, $^{111}$In, $^{201}$Tl, and $^{67}$Ga. As used herein, an "effective amount" is that amount of radionuclide-charcoal sufficient to allow a gastrointestinal or colonic transit profile to be obtained by scintigraphy.

BRIEF DESCRIPTION OF THE FIGURES

FIG. 1 depicts the anterior and posterior scintiscans of $^{99m}$Tc-activated charcoal and $^{111}$In-resin pellets which illustrates the distribution of radioisotope in the colon at 24 hours after ingestion of a delayed-release capsule containing both markers in a healthy volunteer's colon.

DETAILED DESCRIPTION OF THE INVENTION

Figure 2:
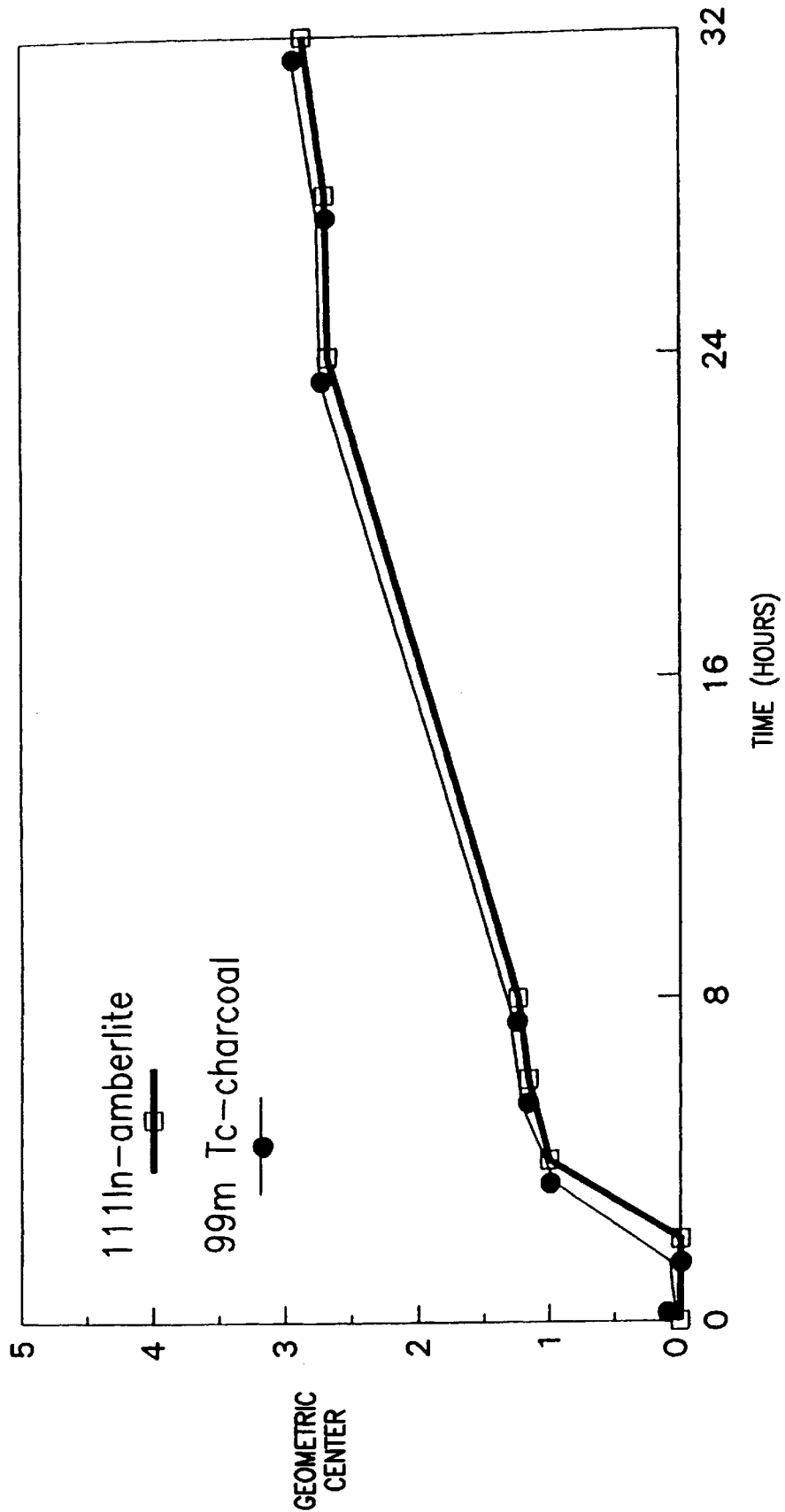
FIG. 2 is a graphical depiction of a time-activity curve of $^{111}$In-Amberlite® pellets and $^{99m}$Tc-activated charcoal in the colon over 32 hours after ingestion. Geometric center 0 represents the ileocolonic junction, 1 represents the hepatic flexure, 2 represents the splenic flexure, 3 represents the end of the descending colon, 4 represents the end of the rectum, and 5 is the stool.

The present invention provides unit dosage forms comprising an effective amount of radionuclide-bound activated charcoal that are not enterically coated, i.e., that release the charcoal in the stomach. Thus, the dosage forms of the present invention can be used to measure motor function of the entire gastrointestinal (g.i.) tract and particularly the colon, which is useful in evaluating patients with abdominal complaints such as irritable bowel, constipation and diarrhea as well as unexplained nausea, vomiting, early satiety, and abdominal pain. These symptom complexes constitute more than 50% of all patients referred to gastroenterologists. There currently is no approved agent/test which can replicate such a noninvasive test of gut motility.

Applicants have made the surprising discovery that the unit dosage form of the present invention is as effective as the currently used resin-based marker for measuring colonic motility while providing an increased ease of use. A particular advantage of the invention is that, because the materials used to manufacture the unit dosage forms of the present invention are all approved by the FDA, there is no need to apply for an IND for the clinical use of the unit dosage form of the present invention.

A. Activated charcoal

Activated charcoal or "activated carbon" is a fine, odorless, tasteless, porous, black powder of about 0.1–0.2 mm particles (pores 2 5 nm) that is free of grittiness. Preferably, 100 mesh (0.15 mm) activated charcoal is used. It is prepared from vegetable matter by carbonization processes intended to confer a high adsorbing power. It is practically insoluble in all usual solvents and is relatively nontoxic in single, 50–100 g administrations at a dilution of 20 g in 240 ml water. It can adsorb a wide range of plant and inorganic poisons and many drugs. It rarely causes vomiting when administered orally. Activated charcoal is approved for use as a medicinal by the FDA, fulfills the USP Standards, and can effectively associate with different radionuclides. See H. W. Davidson et al., *Manufactured Carbon* (Pergamon Press, N.Y., 1968); Smisek et al., *Active Carbon* (Elsevier Pub. Co., Amsterdam, 1970); Merck 1815 (11th ed. 1989).

B. Radioisotopes

Any radioactive element that is approved for administration to humans can be used as the radioisotope in the present invention. Suitable ions include the following: Antimony-124, Antimony-125, Arsenic-74, Barium-103, Barium-140, Beryllium-7, Bismuth-206, Bismuth-207, Cadmium-109, Cadmium-115m, Calcium-45, Cerium-139, Cerium-141, Cerium-144, Cesium-137, Chromium-51, Cobalt-56, Cobalt-57, Cobalt-58, Cobalt-60, Cobalt-64, Erbium-169, Europium-152, Gadolinium-153, Gallium-67, Gold-195, Gold-199, Hafnium-175, Hafnium-175–181, Indium-111, Iridium-192, Iron-55, Iron-59, Krypton-85, Lead-210, Manganese-54, Mercury-197, Mercury-203, Molybdenum-99, Neodymium-147, Neptunium-237, Nickel-63, Niobium-95, Osmium-185, 191, Palladium-103, Platinum-195m, Praseodymium-143, Promethium-147, Protactinium-233, Radium-226, Rhenium-186, Rubidium-86, Ruthenium-103, Ruthenium-106, Scandium-44, Scandium-46, Selenium-75, Silver-100m, Silver-111, Sodium-22, Strontium-85, Strontium-89, Strontium-90, Sulfur-35, Tantalum-182, Technetium-99m, Tellurium-125, Tellurium-132, Thallium-170, Thallium-201, Thallium-204, Thorium-228, Thorium-232, Tin-113, Titanium-44, Tungsten-185, Vanadium-48, Vanadium-49, Ytterbium-169, Yttrium-88, Yttrium-90, Yttrium-91, Zinc-65, and Zirconium-95. Preferably, the radioisotope used in the present invention is metastable technetium-99m ($^{99m}$Tc), thallium 201, gallium 67 or indium 111. A mixture of one or more radionuclide may be used in some cases. As used herein, the term "radionuclide" or "radioisotope" also includes any organic chelating agent that may be associated therewith.

1. $^{99m}$Tc

Metastable technetium ($^{99m}$Tc) is the principle radioisotope used in clinical diagnostic nuclear medicine and is reactor-produced. Specifically, the form of technetium 99m utilized in the present invention is the diethylenetriaminepentaacetic acid chelate of technetium 99m, i.e., $^{99m}$Tc-DTPA.

$^{99m}$Tc-DTPA is prepared by the addition of 2–8 ml sterile $^{99m}$Tc-pertechnetate sodium saline solution (Amersham Healthcare, Medi-Physics, Inc., Arlington Heights, Ill.) to a DTPA reaction vial containing 5 mg pentetate pentasodium and 0.17 mg (min.) stannous chloride as a reducing agent for $^{99m}$Tc-pertechnetate. If sterile conditions are maintained, no further purification is required. DTPA reaction vial (DTPA [chelate] multidose kit) is commercially available from a variety of providers, including Amersham Healthcare, Medi-Physics, Inc., Arlington Heights, Ill.

Although not a true chelate, $^{99m}$Tc-DTPA does not tend to concentrate in any organ as is the case with $^{99m}$Tc-pertechnetate, which follows the pathway of iodide. $^{99m}$Tc-DTPA is uniformly distributed throughout the extracellular space and is rapidly cleared by the kidneys without retention. The compound has previously been used for brain and kidney visualization and for vascular dynamic studies.

2. $^{111}$In

Indium-111 normally exists in aqueous solution in the +3 valence state since indium compounds of lower valencies are unstable. Indium (+3) ions are colorless and resemble aluminum (+3) ions in many ways. The radioisotope is prepared by bombarding a cadmium target with 15 MeV deuterons to produce $^{111}$In. $^{111}$In is then etched from the target with HCl, carrier $Fe^{3+}$ is added and the $^{111}$In is precipitated, along with $Fe(OH)_3$, by adding $NH_4OH$. The precipitate is separated, dissolved in HCl, and the ferric iron removed by extraction with isopropyl ether. $^{111}$In is commercially available from Mallinkrodt (St. Louis, Mo.) and Amersham/Medi-Physics (Arlington Hts, Ill.).

$^{111}$In has been used to tag a variety of compounds, including $^{111}$In-transferrin, which has been used for a replacement for $^{131}$I-HSA, $^{111}$In-EDTA and $^{111}$In-DTPA, useful for cisternography and $^{111}$In-bleomycin, which has been used for tumor localization.

$^{111}$In-DTPA is prepared by adding $^{111}$InCl$_3$ (550–600 $\mu$Ci) injectable solution to 1 mg Na-DTPA in a test tube vortexing the mixture for 2 minutes. Sterile 12.6% anticoagulant citrate dextrose (ACD)/saline solution (6 ml) is added, vortexed and the pH adjusted to 6.5 with 1.0 N NaOH.

3. $^{201}$Tl $^{201}$Tl is prepared by bombarding thallium with protons to produce $^{201}$Pb. The radioactive lead is complexed and the undesirable thallium target material is removed by ion exchange. The lead radioisotopes are then affixed to another column from which $^{201}$Tl is eluted following its formation by decay of $^{201}$Pb. $^{201}$Tl is commercially available from Mallinkrodt (St. Louis, Mo.).

$^{201}$Tl is used in myocardial imaging for diagnosis and localization of myocardial ischemia and infarction. See Angello et al. (U.S. Pat. No. 4,824,660). It is an adjunct to angiography. Thallium mimics potassium ions and is taken up by the cells of the heart; a decrease in the vitality of the cells is indicated by decreased $^{201}$Tl uptake. It has been reported that $^{201}$Tl is also useful for thyroid imaging, in particular for the detection of marked goiter and thyroid carcinoma.

4. $^{67}$Ga

Gallium 67 is produced by proton irradiation of $^{67}$Zn enriched $ZnO_2$. $^{66}$Ga and $^{65}$Ga are formed at the same time, but decay rapidly due to their relatively short half-lives. The resulting $^{67}$Ga is essentially carrier-free. The expiration date of the product is limited by the 78 hour half life of $^{67}$Ga. $^{67}$Ga is available commercially from DuPont (Billerica, Mass.) and Amersham/Medi-Physics.

$^{67}$Ga has been used to diagnose lesions of the lung, breast, maxillary sinuses and liver by using scanning and organ-imaging techniques. In addition, $^{67}$Ga is useful for placental localization and for the identification of certain inflammatory conditions such as pancreatitis or inflammatory bowel disease.

C. Unit Dosage Forms

The present unit dosage forms are preferably prepared using pharmaceutically acceptable carriers adapted for oral administration in solid ingestible dosage forms, or dispersed in a nontoxic liquid carrier, such as an aqueous vehicle, to the desired concentration, and at a pH at which the enteric coating, if any, is stable.

The unit dosage form of the present invention intended to measure colonic transit is preferably enterically coated so that the radioactive marker adsorbed on the activated charcoal (RMAAC) is released from the unit dosage form in the lower intestinal tract, e.g., in the terminal portion of the ileum and in the colon of the patient. As noted above, another embodiment of the invention provides a unit dosage form of the RMAAC for measurement of gut motility that is not enterically coated. In the case of enterically coated dosages, microparticles of the RMAAC may be individually coated and delivered in a suspension in a liquid carrier (vehicle), or may be encapsulated as an enterically coated powder or suspension in a liquid or semi-solid vehicle in hard or soft gelatin capsules. Alternatively, the RMAAC may be encapsulated as a solid or suspension in a hard or soft gelatin capsule that is itself enterically coated. The RMAAC can also be combined with adjuvants employed in solid unit dosage forms, such as fillers and binders, compressed into shaped, solid dosage forms such as pills or tablets, and the pills or tablets treated so as to apply an enteric coating of suitable thickness thereto.

Enteric coatings are those which remain intact in the stomach, but will dissolve and release the contents of the dosage form once it reaches the small intestine. The purpose of an enteric coating is to delay the release of the RMAAC until it reached the target site of action in the colon. Thus, a useful enteric coating is one that remains undissociated in the low pH environment of the stomach, but readily ionizes when the pH rises to about 6–6.5. The most effective enteric polymers are polyacids having a $pK_a$ of 3 to 5.

The most extensively use polymer is cellulose acetate phthalate which is capable of functioning effectively as an enteric coating. However, a pH greater than 6 usually is required for solubility and thus a delay in drug release may ensue. Another useful polymer is polyvinyl acetate phthalate (PVAP) which is less permeable to moisture and gastric fluid, more stable to hydrolysis and able to ionize at a lower pH, resulting in earlier release of actives in the duodenum.

A more recently available polymer is hydroxypropyl methylcellulose phthalate. This has similar stability to PVAP and dissociates in the same pH range.

1. Polymethacrylate Coatings

A further example of currently used polymers are those based on methacrylic acid, e.g., methacrylic acid ester copolymers with acidic ionizable groups. Methacrylic ester monomers have the generic formula $CH_2=C(CH_3)COOR$, wherein R is typically $(C_1-C_{12})$alkyl, and it is the nature of the R group that generally determines the properties of the corresponding polymers. Methacrylates differ from acrylates in that the hydrogen of the acrylate is replaced by a methyl group or other alkyl group. It is the a-methyl group of the polymethacrylate that imparts the stability, hardness, and stiffness to methacrylic polymers. The methacrylate monomers are unusually versatile building blocks since they are moderate-to-high boiling liquids that readily polymerize or copolymerize with a variety of other monomers. All of the methacrylates readily copolymerize with each other and with the acrylate series; thus extreme ranges of properties can be built into the polymer. Furthermore, methacrylate polymers are generally non-toxic. A preferred methacrylate polymer for use in the present invention is available from Rohm Tech, Inc., Malden, Pa. under the designation Eudragit® S-100.

Various systems are available that allow each of these enteric polymers to be applied as aqueous dispersions, thus facilitating the use of aqueous film-coating technology for the enteric coating of pharmaceutical dosage forms.

D. Process of manufacturing the unit dosage forms

The activated charcoal is employed as a carrier for the appropriate amount of radioisotope by addition of the radioisotope to the activated charcoal in normal saline followed by heating for about 0.1–1 hrs with stirring, and subsequent evaporation of the aqueous phase to dryness. For example, in example 1, hereinbelow, activated charcoal was mixed with 8 mCi $^{99m}$Tc-DTPA. Radioisotope dosages were selected to insure optimal colonic imaging up to 32 hours after ingestion.

The charcoal may be mixed with the radioisotope prior to placing it in the capsule and enterically coating the capsule, with a methacrylate solution. Alternatively, the charcoal may first be placed in a gelatin capsule and the radioisotope subsequently injected into the capsule. Therefore, unit dosage forms comprising hard or soft gelatin capsules that are preferably enterically coated and which enclose an amount of activated charcoal effective to measure gut motility are also an aspect of the invention. Preliminary studies show that injection of the radionuclide does not result in early dissolution of the enterically coated capsule in acidic environments. In this manner, the charcoal, can be encapsulated in an enteric-coated capsule and later shipped from the manufacturing site and complexed with the radionuclide in a nuclear medicine facility just before use.

A preselected diagnostic unit dose comprising one or more unit dosage forms is then administered to the test animal or human patient to attain the desired in vivo levels. Doses useful for imaging can be empirically derived, from those found to be effective to image organs in healthy human subjects, such as those described hereinbelow, or from animal models. Typically, unit dosages are 0.001–100 g of radioactive activated charcoal, preferably unit dosages are about 0.01–20 g. Typical unit dosages of radiation ingested are about 1–40 mCi $^{99m}$Tc, and about 10–1000 $\mu$Ci $^{111}$In, about 0.1–10 mCi $^{201}$Tl and about 0.1–20 mCi $^{67}$Ga.

The invention will be further described by reference to the following detailed examples.

EXAMPLE 1
Preparation of Radiolabeled Charcoal or Resin

Activated charcoal (100 mesh, 5 mg, J. T. Baker Chem. Co., Phillipsburg, N.J.) was mixed with 0.2–0.3 ml of the $^{99m}$Tc-DTPA injection solution prepared as disclosed hereinabove, comprising 8 mCi $^{99m}$Tc-DTPA or the 500 μCi of $^{111}$In-DTPA solution, for 15 minutes. The mixture was evaporated to dryness at 90–100° C. $^{201}$TlCl and $^{67}$Ga-citrate were purchased from Mallinckrodt Medical Inc., St. Louis, Mo. as injectable solutions and absorbed onto charcoal by the same procedure.

Amberlite® 120 P resin pellets (1.0 g) (Sigma Chemical Co., St. Louis, Mo.) were radiolabeled with 0.1–0.25 mCi InCl$_3$ in 0.4 N HCl as in previous studies, the beads were rinsed with 0.04 N HCl twice and then dried. Camilleri et al., Am. J. Physiol., 257: G284 (1989). Amberlite® SRA-410 beads (1.0 g) were labeled in normal saline with 1 or 2 mCi: $^{99m}$Tc-DTPA for gastric or small bowel transit tests, respectively, and rinsed twice with normal saline and then with distilled water. Radioisotope dosages were selected to insure optimal colonic imaging up to 32 hours after ingestion.

The radiolabeled particles or dosage of charcoal were then placed into a size 1 hard gelatin capsule which was then coated with Eudragit® S-100, Rohm Tech Inc., Malden, Mass., which dissolves at alkaline pHs that are only achieved in the distal ileum in humans. Fordtran et al., Am. J. Dig Dis., 11:503 (1966); Meltrum et al., Br. Med. J, 2:104 (1972); Evans et al., Gut, 29:1035 (1988).

The capsules were coated by preparing a coating solution of 13 g of the Eudragit® S-100 in a stirred mixture of 31 ml acetone, 46 ml isopropyl alcohol, 2 ml dibutyl phthate and 1.0 ml water, and dipping the filled capsules into the solution twice.

EXAMPLE 2
In Vitro Studies

Samples of 5 mg activated charcoal comprising absorbed $^{99m}$Tc-DTPA, $^{111}$In-DTPA, $^{99m}$Tc-pertechnetate (Per), $^{201}$Tl chloride, $^{67}$Ga citrate, and $^{111}$In chloride were incubated in a milieu that mimicked gastric content with 33 μM pepsin and 0.2 M hydrochloric acid (Thomforde et al., J. Nucl. Med. Tech., 13:11 (1985)) at pH ranging between 2.0 and 4.0, and in a separate milieu that mimicked small intestinal content with lipase and trypsin, each 2000 U/mL, and glycochenodeoxycholate, 1 mM/L, at pH7. Thomforde et al., J. Nucl. Med. Tech., 13:11 (1985). At specified time points, the incubate was spun down, and the amounts of radioisotope adsorbed to the solid charcoal particles and the amount of free radioisotope in the supernatant were determined.

Table I shows the results of association of radioisotopes to activated charcoal. Under all chemical conditions and, particularly, in a wide pH range mimicking the intraluminal pHs in the gut, the radioisotopes were efficiently and persistently adsorbed onto the activated charcoal.

TABLE I
ACTIVATED CHARCOAL STUDY WITH DIFFERENT RADIOPHARMACEUTICALS AT DIFFERENT TIMES (n = 3)

| Incubation Time | Lipase + Trypsin + Glycochenodeoxycholic acid pH = 7.2 | | | | | |
|---|---|---|---|---|---|---|
| | $^{99m}$Tc-Per | $^{99m}$Tc-DTPA | $^{111}$InCl$_3$ | $^{111}$In-DTPA | $^{201}$TlCl | $^{67}$Ga citrate |
| 0 min | 100.0 ± 0.0 | 100.0 ± 0.0 | 100.0 ± 0.0 | 100.0 ± 0.0 | 100.0 ± 0.0 | 50.0 ± 1.4 |
| 90 min | 100.0 ± 0.0 | 100.0 ± 0.0 | 100.0 ± 0.0 | 100.0 ± 0.0 | 100.0 ± 0.0 | 45.6 ± 2.1 |
| 1 hr | 100.0 ± 0.0 | 100.0 ± 0.0 | 100.0 ± 0.0 | 100.0 ± 0.0 | 100.0 ± 0.0 | 42.0 ± 1.8 |
| 1 hr 30 min | 100.0 ± 0.0 | 100.0 ± 0.0 | 100.0 ± 0.0 | 100.0 ± 0.0 | 100.0 ± 0.0 | 44.1 ± 2.3 |
| 2 hr | 100.0 ± 0.0 | 100.0 ± 0.0 | 100.0 ± 0.0 | 100.0 ± 0.0 | 100.0 ± 0.0 | 45.7 ± 5.0 |
| 2 hr 30 min | 100.0 ± 0.0 | 100.0 ± 0.0 | 99.6 ± 0.1 | 100.0 ± 0.0 | 100.0 ± 0.0 | 43.2 ± 1.1 |
| 3 hr | 100.0 ± 0.0 | 100.0 ± 0.0 | 99.9 ± 0.3 | 100.0 ± 0.0 | 100.0 ± 0.0 | 46.7 ± 2.3 |

| Incubation Time | Pepsin + HCl pH = 2.4 | | | | | |
|---|---|---|---|---|---|---|
| | $^{99m}$Tc-Per | $^{99m}$Tc-DTPA | $^{111}$InCl$_3$ | $^{111}$In-DTPA | $^{201}$TlCl | $^{67}$Ga citrate |
| 0 min | 100.0 ± 0.0 | 100.0 ± 0.0 | 100.0 ± 0.0 | 100.0 ± 0.0 | 100.0 ± 0.0 | 58.9 ± 7.1 |
| 90 min | 100.0 ± 0.0 | 100.0 ± 0.0 | 100.0 ± 0.0 | 100.0 ± 0.0 | 100.0 ± 0.0 | 74.1 ± 1.4 |
| 1 hr | 100.0 ± 0.0 | 100.0 ± 0.0 | 100.0 ± 0.0 | 100.0 ± 0.0 | 100.0 ± 0.0 | 72.6 ± 1.2 |
| 1 hr 30 min | 100.0 ± 0.0 | 100.0 ± 0.0 | 100.0 ± 0.0 | 100.0 ± 0.0 | 100.0 ± 0.0 | 71.7 ± 0.8 |
| 2 hr | 100.0 ± 0.0 | 100.0 ± 0.0 | 100.0 ± 0.0 | 100.0 ± 0.0 | 100.0 ± 0.0 | 74.4 ± 0.8 |
| 2 hr 30 min | 100.0 ± 0.0 | 100.0 ± 0.0 | 100.0 ± 0.0 | 100.0 ± 0.0 | 100.0 ± 0.0 | 71.0 ± 1.8 |
| 3 hr | 100.0 ± 0.0 | 100.0 ± 0.0 | 100.0 ± 0.0 | 100.0 ± 0.0 | 100.0 ± 0.0 | 68.2 ± 1.0 |

EXAMPLE 3
Performance of In Vivo Transit Studies

Ten healthy volunteers (5 men, 5 women) in the age range of 18 to 60 years, who were not taking any medication on a chronic basis, were recruited by public advertisement. All signed written informed consent of the research protocol which was approved by Mayo's Institutional Review Board and Radiation Control Committee. All volunteers were screened for gastrointestinal symptoms by means of a validated questionnaire developed for identification of functional gastrointestinal diseases. Talley et al., Ann. Intern. Med., 111:671 (1989). All female participants had previously undergone sterilization or had a negative pregnancy test within 48 hours of receiving the radiolabels.

Participants attended the General Clinical Research Center Physiology Core Laboratory at St. Marys Hospital after an overnight fast. A capsule containing a 10 mg dose of resin—$^{111}$In or 2 mg of activated charcoal—$^{99m}$Tc was ingested at time 0, patients ate meals ad libitum and dual (anterior and posterior) gamma camera scans (GE Starcam, Milwaukee, Wis.) were obtained with the subject standing at 0, 2, 4, 6, 8, 24, 28, and 32 hours after ingestion of the capsule.

All subjects completed the studies without complications. All scans were obtained as planned except for two subjects (#9 and #10) who were unable to attend the laboratory for the final scan at 32 hours. FIG. 1 shows an example of colonic silhouettes containing $^{99m}$Tc charcoal and $^{111}$In ion exchange resin pellets. The distribution of radioisotope at 24 and 32 hours is shown to be similar with the two radioisotopes. FIG. 2 shows a comparison of the time-activity curve for colonic radioactivity for the two markers. The curves are virtually identical.

A region of interest program was used to estimate the amount of radioactivity in the ascending, transverse, descending, sigmoid and rectum, and stool. These were designated as regions 1 to 5 respectively for estimating the geometric center of counts for colonic transit, as in previous studies. See, for example, Stivland et al., *Gastroenterology*, 101:107 (1991); Proano et al., *Am. J. Physiol.*, 258:G856 (1990); Camilleri et al., *Gastroenterology*, 103:3 (1992); Charles et al., *Mayo Clin. Proc.*, 70:113 (1995) and Vassallo et al., *Gastroenterology*, 102:102 (1992). The geometric mean of anterior and posterior counts was estimated and, for each region, the proportion of radioisotope in the region was estimated by dividing the counts in that region by the total counts of radioactivity in the entire colon. For $^{99m}$Tc counts, crossover from the $^{111}$In window was first estimated and subtracted from the total counts using a downscatter factor of 0.8. A geometric center (weighted average of counts) was calculated as a summary of the transit profile for each radioisotope at 4, 6, 8, 24, 28, and 32 hours.

In order to be deemed equally accurate and therefore applicable clinically, the radiolabeled activated charcoal profile would need to have a transit profile that varied by less than 10% from radiolabeled ion exchange resin pellets. A sample size of 10 provided >80% power to detect such an agreement between the two markers at $\alpha=0.05$.

The data were first plotted as geometric center at each time point to assess intraindividual differences in transit profile using the two markers. Second, the differences in geometric center at each time point were plotted, and the 95% confidence intervals were plotted on either side of the median acta. If the confidence interval range did not overlap with a difference in geometric center of zero, it would suggest that the colonic transit profiles of the two markers were different.

Figure 3:
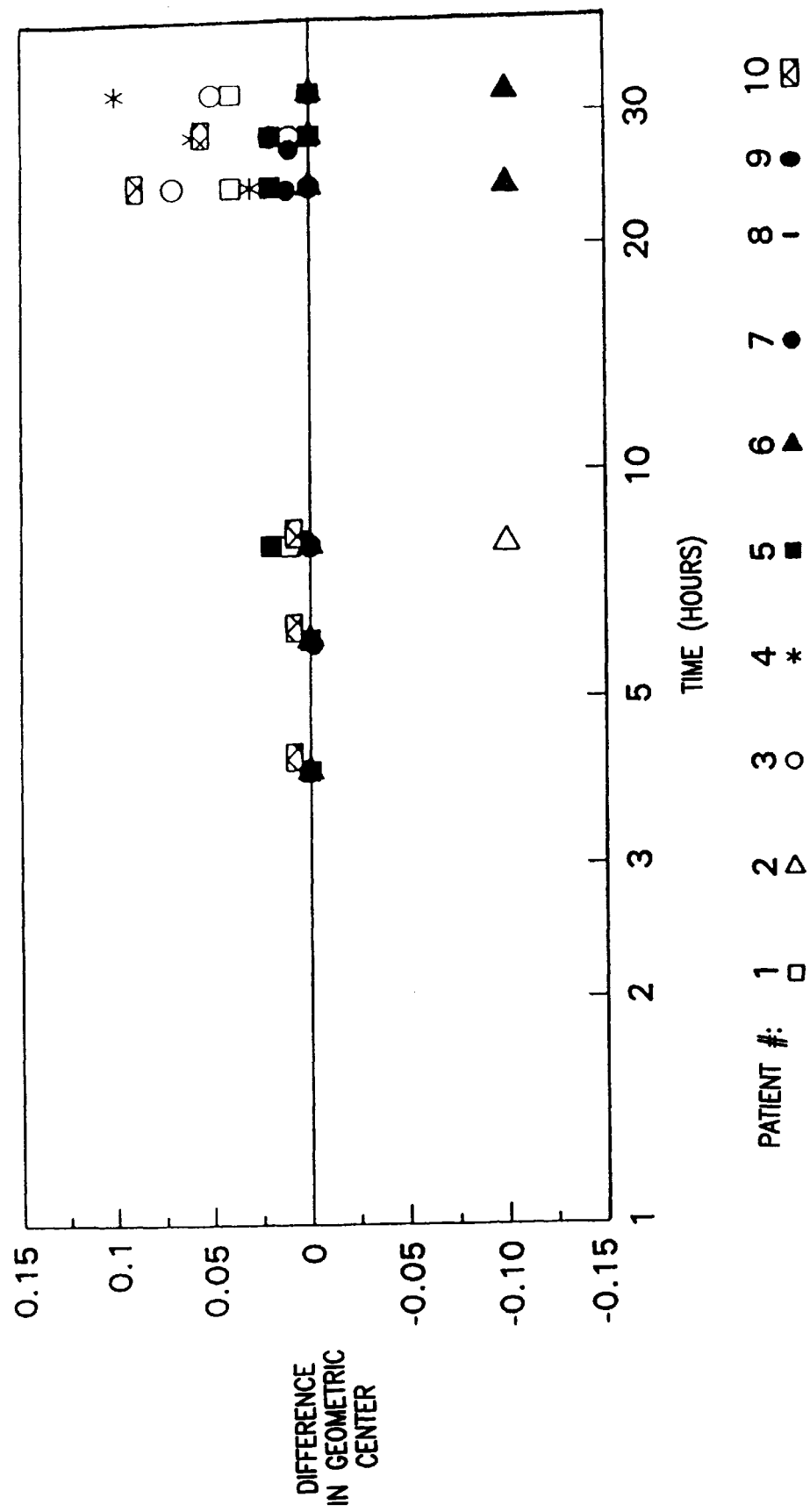
FIG. 3 illustrates the difference in geometric center of $^{99m}$Tc-activated charcoal and $^{111}$In-pellets at scan times for each individual identified by a different symbol.
Figure 4:
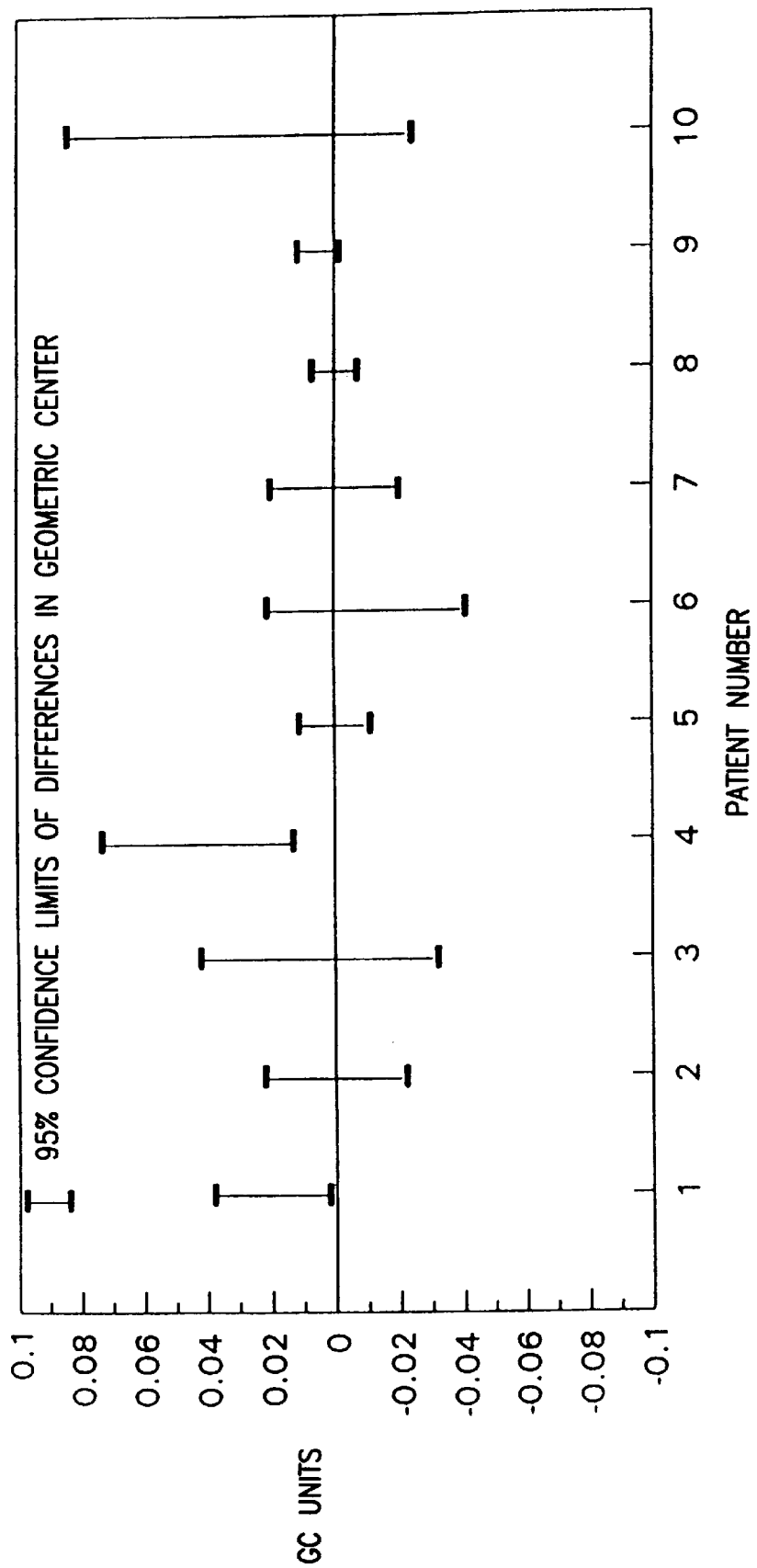
FIG. 4 illustrates the variance of difference in geometric center of $^{99m}$Tc-activated charcoal and $^{111}$In-pellets at scan times in 10 healthy participants.

FIG. 3 plots the difference in geometric center at the different times of imaging. Note that the highest difference in geometric center units observed was 0.1, which represents 10% or less of one of the colonic regions studied. FIG. 4 plots the 95% confidence limits above and below the median difference in geometric center at each scanning time. The overlap of each of 10 of the variances with the zero difference line, negates the null hypothesis that the transit profiles of the two markers were significantly different.

This study shows that the transit profiles through the colon of $^{99m}$Tc-RMACA and $^{111}$In ion exchange resin pellets in healthy adult human participants were virtually indistinguishable. The normal profile of activated charcoal particles suggests that the adherence of the charcoal itself to intracolonic residue was greater than its adherence to the colonic mucosa. This was an important consideration since the marker must reflect movement of intracolonic residue to be useful for measuring colonic transit.

Activated charcoal is not ionically charged and, therefore, does not bind to ion exchange resin pellets in vitro. Therefore, the similarity of the transit profiles does not merely reflect binding of charcoal to the pellets, but it likely reflects similar movement of both markers as part of the intracolonic residue. Charcoal may also be advantageous over the pellets since it binds to vegetable residue by virtue of its high adsorptive power and therefore actually traverses the colon with endogenous residues.

Another potential pitfall to be considered is that $^{99m}$Tc might be bound to the ion exchange resin pellets. This is unlikely since the ion exchange resin pellets used were cation binders, whereas $^{99m}$Tc was part of an anion (pertechnetate). The in vitro studies suggest that the high adsorption and retention of radioisotope on the activated charcoal particles insured that the radioisotope was retained in the charcoal throughout its transit through the colon. Similarly, the excellent binding characteristics of $^{111}$In to ion exchange pellets make it highly unlikely that $^{111}$In dissociated from the ion exchange pellets and adsorbed onto the charcoal or to other particles in the colonic residue.

Activated charcoal binds medications and some nutrients, and this might be disadvantageous if the charcoal mixed with food constituents in the stomach or small bowel. However, since the charcoal carrier of the radioisotope is given in small quantities (5 mg or less), and the charcoal is encapsulated throughout its passage through most of the small intestine by the enteric coated capsule, the likelihood of any deleterious effect of the charcoal on nutrient or medication absorption is negligible. Moreover, since the method is being developed as a test, it is unlikely that most patients would require more than occasional ingestion of the activated charcoal for measurement of colonic transit.

Since colonic transit profiles can be accurately assessed over a 24-hour period (Camilleri et al., *Gastroenterology*, 103:3 (1992)), the starting dose of $^{99m}$Tc can probably be reduced to 4 or 5 mCi with adequate counts for accurate measurements. At this dose, $H_E$ is 360 mrad, and organ exposures are summarized in Table II.

TABLE II

RADIATION EXPOSURE (mrad) WITH 4 mCi $^{99m}$Tc-ACTIVATED CHARCOAL

| Activity | Body | Stomach | SI | ULI | LLI | Marrow | Gonads | $H_E$ |
|---|---|---|---|---|---|---|---|---|
| 4 mCi | 72 | 960 | 960 | 1840 | 1120 | 536 | 336 | 360 |

All patents and publications are incorporated by reference herein, as though individually incorporated by reference. While only certain preferred embodiments of this invention have been shown and described by way of illustration, many modifications will occur to those skilled in the art and it is, therefore, desired that it be understood that this is intended herein to cover all such modifications that fall within the spirit and scope of this invention.

What is claimed is:

1. A method of measuring colonic motility, said method comprising:
   (a) administering to a subject, a unit dosage form comprising an effective amount of a radioisotope adsorbed on activated charcoal; and (b) employing scintigraphy to measure the colonic transit of said radioisotope.

2. The method of claim 1 wherein the radioisotope is selected from the group consisting of $^{99m}$Tc, $^{111}$In, $^{201}$Tl, and $^{67}$Ga.

3. The method of claim 1 wherein the subject is a human.

4. The method of claim 1 wherein the unit dosage form comprises about 0.01–20 g activated charcoal.

5. The method of claim 1 wherein the unit dosage form is enterically coated.

6. The method of claim 1 wherein the radioisotope-bound activated charcoal is enterically coated.

7. The method of claim 5 wherein the radioisotope-activated charcoal is enclosed in an enterically coated gelatin capsule.

8. The method of claim 5 wherein the radioisotope-activated charcoal is formed into an enterically coated tablet.

\* \* \* \* \*